(12) United States Patent
Omidbakhsh et al.

(10) Patent No.: US 9,233,180 B2
(45) Date of Patent: *Jan. 12, 2016

(54) HYDROGEN PEROXIDE DISINFECTANT CONTAINING A CYCLIC CARBOXYLIC ACID AND/OR AROMATIC ALCOHOL

(71) Applicant: VIROX TECHNOLOGIES INC., Oakville (CA)

(72) Inventors: Navid Omidbakhsh, Fairfax, VA (US); Jose A. Ramirez, Vernon Hills, IL (US)

(73) Assignee: VIROX TECHNOLOGIES INC., Oakville, Ontario (CA)

(*) Notice: Subject to any disclaimer, the term of this patent is extended or adjusted under 35 U.S.C. 154(b) by 0 days.

This patent is subject to a terminal disclaimer.

(21) Appl. No.: 14/056,117

(22) Filed: Oct. 17, 2013

(65) Prior Publication Data

US 2014/0044596 A1 Feb. 13, 2014

Related U.S. Application Data

(63) Continuation of application No. 13/476,212, filed on May 21, 2012, now abandoned, which is a continuation of application No. 12/068,575, filed on Feb. 8, 2008, now abandoned, which is a continuation-in-part of application No. 10/712,990, filed on Nov. 17, 2003, now Pat. No. 7,354,604.

(60) Provisional application No. 60/426,306, filed on Nov. 15, 2002.

(51) Int. Cl.
| | |
|---|---|
| A01N 59/00 | (2006.01) |
| A01N 25/30 | (2006.01) |
| A01N 25/02 | (2006.01) |
| A01N 37/02 | (2006.01) |
| A01N 37/36 | (2006.01) |
| A61L 2/18 | (2006.01) |
| A01N 31/04 | (2006.01) |

(52) U.S. Cl.
CPC ............... *A61L 2/186* (2013.01); *A01N 31/04* (2013.01); *A01N 59/00* (2013.01)

(58) Field of Classification Search
CPC ....... A01N 59/00; A01N 25/30; A01N 25/02; A01N 25/22; A01N 31/04; A01N 37/36; A01N 37/02; A01N 41/04; A01N 2300/00; A61K 8/466; A61K 8/22; A61K 31/60; A61K 31/31; A61K 31/34; A61K 33/40; A61Q 19/00; A61Q 19/007; C11D 3/3454; C11D 3/3947; C11D 3/43; C11D 3/48; C11D 3/2075; Y10S 424/06; Y10S 514/97
See application file for complete search history.

(56) References Cited

U.S. PATENT DOCUMENTS

| | | |
|---|---|---|
| 3,969,258 A | 7/1976 | Carandang et al. |
| 4,051,058 A | 9/1977 | Bowing et al. |
| 4,051,059 A | 9/1977 | Bowing et al. |
| 4,405,482 A | 9/1983 | Hayes et al. |
| 4,446,153 A | 5/1984 | Yang |
| 4,477,438 A | 10/1984 | Willcockson et al. |
| 4,518,585 A | 5/1985 | Greene et al. |
| 4,525,291 A | 6/1985 | Smith et al. |
| 4,525,292 A | 6/1985 | Cushman et al. |
| 4,557,898 A | 12/1985 | Greene et al. |
| 4,637,899 A | 1/1987 | Kennedy, Jr. |
| 4,878,951 A | 11/1989 | Pochard et al. |
| 5,059,417 A | 10/1991 | Williams et al. |
| 5,149,463 A | 9/1992 | Peterson |
| 5,171,564 A | 12/1992 | Nathoo et al. |
| 5,200,189 A | 4/1993 | Oakes et al. |
| 5,205,960 A | 4/1993 | Kristopeit et al. |
| 5,244,593 A | 9/1993 | Roselle et al. |
| 5,264,229 A | 11/1993 | Mannig et al. |
| 5,376,387 A | 12/1994 | Monticello |
| 5,387,605 A | 2/1995 | Beilfuss et al. |
| 5,523,012 A | 6/1996 | Winterton et al. |
| 5,599,400 A | 2/1997 | Mao et al. |

(Continued)

FOREIGN PATENT DOCUMENTS

| | | |
|---|---|---|
| CA | 1102502 | 6/1981 |
| CA | 1244759 | 11/1988 |

(Continued)

OTHER PUBLICATIONS

Dow, Product Safety Assessment, Primary Amyl Acetate, Dec. 23, 2014, p. 1-6.*
Database WPI, Week 199615, Derwent Publications Ltd., London, GB, 1996-149587, XP002287351 (Biol Instr Mfr Res Inst) Jul. 27, 1995.
XP002287349: SS. Block "Disinfection, Sterilization and Preservation" G.R. Dychdala et al., Chapter 14: Surface-Active Agents: Acidic Anionic Compounds; pp. 256-262; 1991.

(Continued)

*Primary Examiner* — John Pak
*Assistant Examiner* — Nathan W Schlientz
(74) *Attorney, Agent, or Firm* — Clark & Brody

(57) ABSTRACT

An aqueous disinfecting solution, a concentrated version of the solution, and a dry powdered composition which may be dissolved in water to provide the solution. The solution has a pH of from 0.6 to 7 and comprises (a) hydrogen peroxide in a concentration of from 0.01 to 6% w/w; and (b) at least one component chosen from cyclic carboxylic acids and aromatic alcohols, in a concentration of from 0.01 to 10% w/w, all based on the total weight of the solution. The cyclic carboxylic acids are preferably 2-furan carboxylic acid, benzoic acid and salicylic acid and the aromatic alcohol is preferably benzyl alcohol. Furthermore, the solution may contain surfactants, corrosion inhibitors, hydrotropes, cation sequestering agents, hydrogen peroxide stabilizers, solvents, thickeners, skin conditioning agents, antifoams, and pH buffers.

18 Claims, No Drawings

(56) References Cited

U.S. PATENT DOCUMENTS

| | | | |
|---|---|---|---|
| 5,602,090 | A | 2/1997 | Melikyan et al. |
| 5,641,530 | A | 6/1997 | Chen |
| 5,718,910 | A | 2/1998 | Oakes et al. |
| 5,723,400 | A | 3/1998 | Morini et al. |
| 5,723,406 | A | 3/1998 | Larose et al. |
| 5,736,498 | A | 4/1998 | Gray |
| 5,736,582 | A | 4/1998 | Devillez |
| 5,827,542 | A | 10/1998 | Miner et al. |
| 5,855,217 | A | 1/1999 | John |
| 5,891,392 | A | 4/1999 | Monticello et al. |
| 5,900,256 | A | 5/1999 | Scoville, Jr. et al. |
| 6,043,209 | A | 3/2000 | Micciche et al. |
| 6,096,348 | A | 8/2000 | Miner et al. |
| 6,110,883 | A | 8/2000 | Petri et al. |
| 6,165,957 | A | 12/2000 | Vitomir |
| 6,296,880 | B1 | 10/2001 | Murad |
| 6,309,470 | B1 | 10/2001 | Schulhoff et al. |
| 6,346,279 | B1 | 2/2002 | Rochon |
| 6,383,523 | B1 | 5/2002 | Murad |
| 6,444,636 | B1 | 9/2002 | Toussaint et al. |
| 6,479,454 | B1 | 11/2002 | Smith et al. |
| 6,593,283 | B2 | 7/2003 | Hei et al. |
| 6,617,294 | B2 | 9/2003 | Narula et al. |
| 6,627,589 | B1 | 9/2003 | Arvanitidou |
| 6,803,057 | B2 | 10/2004 | Ramirez et al. |
| 6,841,090 | B1 | 1/2005 | Allighieri et al. |
| 6,927,237 | B2 | 8/2005 | Hei et al. |
| 7,354,604 | B2 | 4/2008 | Ramirez et al. |
| 7,632,523 | B2 | 12/2009 | Ramirez et al. |
| 2002/0072288 | A1 | 6/2002 | Hei et al. |
| 2002/0168422 | A1 | 11/2002 | Hei et al. |
| 2003/0161891 | A1 | 8/2003 | Ruiter |
| 2003/0181377 | A1 | 9/2003 | Hallahan et al. |
| 2003/0203035 | A1 | 10/2003 | Hasan et al. |
| 2003/0206965 | A1 | 11/2003 | Hasan et al. |
| 2003/0228996 | A1 | 12/2003 | Hei et al. |
| 2004/0033923 | A1 | 2/2004 | McClung |
| 2004/0137077 | A1 | 7/2004 | Ancira et al. |
| 2004/0171687 | A1 | 9/2004 | Kemp et al. |
| 2004/0182793 | A1 | 9/2004 | Owens |
| 2005/0019421 | A1 | 1/2005 | Hobbs et al. |
| 2005/0058719 | A1 | 3/2005 | Ramirez et al. |
| 2005/0133460 | A1 | 6/2005 | McClung |
| 2005/0145824 | A1 | 7/2005 | McClung |
| 2005/0145825 | A1 | 7/2005 | McClung |
| 2005/0145826 | A1 | 7/2005 | McClung |
| 2005/0255172 | A1 | 11/2005 | Omidbakhsh |
| 2006/0172911 | A1 | 8/2006 | McClung |
| 2006/0199206 | A1 | 9/2006 | Wang et al. |
| 2006/0285995 | A1 | 12/2006 | Hobbs et al. |

FOREIGN PATENT DOCUMENTS

| | | |
|---|---|---|
| DE | 3229097 | 2/1984 |
| DE | 2629081 | 6/1987 |
| DE | 3543500 | 6/1987 |
| EP | 0057153 | 1/1982 |
| EP | 0087049 | 11/1986 |
| EP | 0252278 | 6/1987 |
| EP | 0289463 | 4/1988 |
| EP | 0351772 | 7/1989 |
| EP | 0456272 | 5/1991 |
| EP | 0524150 | 7/1992 |
| EP | 0505935 | 9/1992 |
| EP | 0582359 | 2/1994 |
| EP | 0582360 | 2/1994 |
| EP | 0776613 | 6/1997 |
| EP | 0845526 | 11/1997 |
| EP | 0 776 613 | 6/1999 |
| EP | 1369037 | 12/2003 |
| EP | 1374679 | 1/2004 |
| GB | 1584170 | 2/1981 |
| GB | 2101350 | 5/1982 |
| JP | 57-192302 | 8/1982 |
| JP | 10-121097 | 5/1988 |
| JP | 9-87677 | 3/1997 |
| JP | 10-130693 | 5/1998 |
| JP | 2001-072503 | 3/2001 |
| WO | WO93/04664 | 3/1993 |
| WO | WO93/14183 | 7/1993 |
| WO | WO95/04001 | 2/1995 |
| WO | WO97/28691 | 8/1997 |
| WO | WO98/11777 | 3/1998 |
| WO | WO98/18894 | 5/1998 |
| WO | WO98/21305 | 5/1998 |
| WO | WO98/59028 | 12/1998 |
| WO | WO99/02638 | 1/1999 |
| WO | WO99/03446 | 1/1999 |
| WO | 99/19441 | 4/1999 |
| WO | WO99/27066 | 6/1999 |
| WO | WO99/52360 | 10/1999 |
| WO | WO00/27981 | 5/2000 |
| WO | WO02/055647 | 7/2002 |
| WO | WO03/005817 | 1/2003 |
| WO | WO03/005818 | 1/2003 |
| WO | WO03/067989 | 8/2003 |
| WO | WO03/076560 | 9/2003 |
| WO | WO2004/035718 | 4/2004 |
| WO | WO2004/045281 | 6/2004 |

OTHER PUBLICATIONS

XP002287350: Database Chemlabs Chemical Abstract Service; Columbus, OH; retrieved from STN-International; Database accession No. 136:351642; abstract. Copyright 2004.

Database WPI, Week 199918, Derwent Publications Ltd., London, GB, 1999-205420, XP002287352 (L Wang) Dec. 16, 1998.

MGC Baldry, "The Bactericidal, Fungicidal and Sporicidal Properties of Hydrogen Peroxide and Peractetic Acid"; Journal of Applied Bacteriology; pp. 417-423; 1982.

Parker et al., "Food Plant Sanitation: Effective Detergency and Cleaning Practice" (New York, Reinhold Publishing Corporation, 1962); pp. 223-263.

"Announcement" (1999) The Canadian Journal of Infection Control; vol. 14, No. 1.

J.A. Lopes, "Evolution of Dairy and Food Plant Sanitizers Against *Salmonella typhimurium* and Listeria Momocytogenes"; Journal of Dairy Science, 1969; pp. 2791-2796.

S.A. Sattar, et al. A Product Based on Accelerated and Stabilized Hydrogen Peroxide, Evidence for Broad-Spectrum Germicidal Activity; (1998)The Canadian Journal of Infection Control.

Dowfax™ Hydrotope Solution: Copyright The Dow Chemical Company (1995-2006): http://www.dow.com/furfactants/products/alkyl_sa.htm.

\* cited by examiner

HYDROGEN PEROXIDE DISINFECTANT CONTAINING A CYCLIC CARBOXYLIC ACID AND/OR AROMATIC ALCOHOL

CROSS-REFERENCE

This application is a continuation of application Ser. No. 13/476,212, filed on May 21, 2012, which is a continuation of application Ser. No. 12/068,575, filed Feb. 8, 2008, which is a continuation-in-part of application Ser. No. 10/712,990, filed Nov. 17, 2003, which claims the benefit of provisional application No. 60/426,306, filed Nov. 15, 2002, all of which are incorporated herein by reference.

FIELD OF THE INVENTION

The present invention relates to acidic aqueous hydrogen peroxide-based disinfecting or sanitizing solutions.

BACKGROUND TO THE INVENTION

In infection control practice, mycobacterial species are typically used as the benchmark for evaluating the potency of a germicide. If a chemical disinfectant is effective in destroying mycobacteria, then it will be judged effective for use as a hard surface disinfectant, against all possible bacterial species and lipophylic and hydrophilic viral particles. For example, in dental practice, a disinfectant registered with the EPA as a tuberculocide is recommended for general hard surface disinfection (CDC, 1993).

Very few liquid chemical disinfectants are effective sporicides, particularly in cold soaking instruments sensitive to chemical attack. The most widely used sporicidal chemical solutions are based on aldehydes, short chain alcohols, phenolic compounds, and certain peroxygens. Aldehydes (e.g. formaldehyde and glutaraldehyde), although highly effective, suffer from serious occupational safety and environmental disposal hazards. Of the peroxygens, peracids are those most widely used in liquid form. Peracetic and performic acids have been marketed for the disinfection of semicritical and critical instruments; however, their aggressive chemical nature tend to damage surfaces and instruments with prolonged use.

Alcohol or phenolic compounds which exhibit good efficacy against mycobacterial species are typically not effective in destroying bacterial endospores. Mycobactericidal products that are based on short-chain alcohols typically contain these ingredients at high concentrations (usually higher than 20% w/w). This makes the products highly flammable and toxic. Furthermore, they are often characterized by a strong alcoholic odor and are therefore difficult to use in large quantities in small enclosed spaces by chemically sensitive individuals. Phenolic compounds can be used by themselves or in combination with other germicidal actives (such as with quaternary ammonium compounds and solvents), in order to achieve wide spectrum efficacy. These compounds are also highly volatile and exhibit strong objectionable odors.

Hypochlorite solutions and other chlorine-based compounds are effective against both mycobacteria and bacterial endospores; however, they are easily inactivated by the presence of organic matter, are unstable when diluted, have a strong, objectionable, chlorinated smell, and are highly corrosive and therefore damaging to most instruments and surfaces.

Aqueous chemical disinfectants are used in applications where, due to occupational, environmental, or toxicological concerns, solvent-based solutions cannot be used. While there are a large number of disinfecting and sanitizing solutions available in the marketplace, there is still a need for a low-volatility, low toxicity, non-corrosive, non-irritating, and stable aqueous disinfectant which is effective against hydrophilic viruses, acid-fast bacteria and bacterial endospores. The present invention is intended to at least partially address this need.

SUMMARY OF THE INVENTION

The present invention provides, in accordance with a first aspect, aqueous, acidic, hydrogen peroxide based solutions, embodiments of which can be, surprisingly, highly effective against mycobacteria and bacterial endospores. Solutions according to the present invention have a pH of from 0.6 to 7 or from 0.6 to 5. Some embodiments of the present inventive solution may have a pH of from 1.9 to 2.1, while other embodiments may have a pH of from 2 to 4 or from 4 to 5.

The present inventive solutions comprise (a) hydrogen peroxide in a concentration of from 0.01 to 6, or from 0.25 to 4% w/w; and (b) at least one component chosen from cyclic carboxylic acids and aromatic alcohols in a concentration of from, 0.01 to 40%, 0.01 to 10% w/w, 0.01 to 8% w/w, 0.1 to 4% w/w, 0.1 to 2.5% w/w, 0.25 to 1.0% w/w, or from 0.4 to 0.6% w/w, all based on the total weight of the solution. The cyclic carboxylic acid is preferably 2-furan carboxylic acid (also referred to herein as 2-furoic acid), benzoic acid and salicylic acid. The aromatic alcohol is preferably benzyl alcohol.

To achieve the desired pH values, the solution may contain acid or alkaline buffers such as phosphoric acid, citric acid, glycolic acid, lactic acid, sodium carbonate, calcium carbonate, sodium carbonate, potassium hydroxide, sodium hydroxide, and ethanolamine.

In one embodiment, the solution may further comprise at least one nonionic surfactant in a concentration of from 0.005 to 3% w/w, 0.01 to 3% w/w, 0.01 to 1% w/w, or from 0.04 to 0.06% w/w, based on the total weight of the solution. Furthermore, the at least one nonionic surfactant is preferably chosen from (a) ethoxylated alcohols and alkylglycosides having a hydrophile lyophile balance from 5 to 15, which may be a C6-C10 alkyl, 3.5 moles of ethylene oxide (EO) alcohol ethoxylate; and (b) a sufficiently water-soluble block copolymer of ethylene oxide and/or propylene oxide.

In yet another embodiment, the solution may further comprise at least one cation sequestering agent in a concentration of from 0.01 to 6% w/w, preferably from 0.05 to 2% w/w, more preferably from 0.1 to 2% w/w, and even more preferably from 0.5 to 1% w/w, based on the total weight of the solution. The cation sequestering agent may be 1-hydroxyethylidene-1,1-diphosphonic acid In still another embodiment of the invention, the solution may contain at least one anionic surfactant chosen from (a) C8-C16 alkyl benzene sulfonic acids and alkali metal, alkaline earth metal, ammonium or alkylamine salts thereof; (b) C8-C18 alkyl sulfonic acids and alkali metal, alkaline earth metal, ammonium or alkylamine salts thereof; (c) C8-C16 alkyl sulfates; and (d) C6-C12 alkyl diphenyl sulfonic acids and alkali metal, alkaline earth metal, ammonium or alkylamine salts thereof, (e) alkyl or alkenyl esters or diesters of sulfosuccinic acid in which the alkyl or alkenyl groups independently contain from six to eighteen carbon atoms and alkali metal, ammonium, calcium and magnesium salts thereof, in a concentration of from 0.01 to 10% w/w, 0.01 to 6% w/w, 0.01 to 5% w/w, 0.01 to 3% w/w, 0.05 to 3% w/w, 0.05 to 2% w/w, 0.05 to 1.5% w/w, or from 0.05 to 1% w/w, all based on the total weight of the solution. The at least one anionic surfactant may be an alkyl benzene sulfonic acid (e.g. dodecyl benzene sulfonic acid), a C6-C12 alkyl diphenyl sulfonate (e.g. C6 alkylated sulfonated diphenyl oxide sodium salt, C10 alkylated sulfonated diphenyl oxide sodium salt), and an alkyl ester of sulfosuccinic acid or salt thereof (e.g. sodium dioctyl sulfosuccinate). The addition of a C6-C12 alkyl diphenyl oxide sulfonate surfactant (e.g. C10 alkylated sulfonated diphenyl oxide sodium salt) has been found to impart to the solution activity against resistant, hydrophilic viruses.

Solutions according to the present invention may comprise at least one corrosion inhibitor in a concentration of from 0.001 to 15% w/w, 0.001 to 5% w/w, 0.01 to 1% w/w, 0.01 to 0.5% w/w, or 0.02 to 0.22% w/w, based on the total weight of the solution. The at least one corrosion inhibitor may be chosen from 1,2,3 benzotriazole, sodium molybdate, sodium nitrite, sodium bisulfate, sodium metabisulfate, chromates, borates, phosphates, polyphosphates, sodium benzoate, sodium silicate and sodium gluconate.

The solution may further contain a hydrotrope in a concentration of from 0.01 to 15% w/w, based on the total weight of the solution. Non-limiting examples of hydrotropes include sodium xylene sulfonate, sodium cumene sulfonate, sodium toluene sulfonate.

Furthermore, the solution may include from 0.01 to 20% w/w of a solvent such as a glycol or glycol ether (e.g. propylene glycol, ethylene glycol, propylene glycol, diethylene glycol, dipropylene glycol), n-butanol, n-butyl acetate, diisobutyl ketone, isobutanol, isobutyl acetate, isopropanol (anhydrous), isopropyl acetate, methyl isobutyl carbinol, methyl isobutyl ketone, primary amyl acetate mixed isomers, n-propanol, npropyl acetate, n-butyl propionate, n-pentyl propionate, ethanol, propyl alcohol and isopropyl alcohol, glycerin.

Furthermore, the solution may include from 0.005% w/w to 5% w/w of antifoams, where the antifoam can be selected from silicone-based antifoams or any antifoam chemical compatible with the solution.

The water used in solutions according to the invention may be tap water, deionized water, or a mixture thereof.

The invention provides, in accordance with a second aspect, a concentrated aqueous, acidic disinfecting solution which may be diluted with water to provide a solution according to the first aspect of the invention. Such solution may have a total cyclic carboxylic acid and aromatic alcohol concentration of up to 30% w/w, based on the total weight of the solution.

The invention provides, in accordance with a third aspect, a dry particulate composition dissolvable in water to produce an aqueous disinfecting solution according to the first or second aspects of the invention. In such embodiments, the composition comprises at least one hydrogen peroxide releasing component, which may be chosen from sodium percarbonate, sodium perborate monohydrate, and sodium perborate tetrahydrate.

In accordance with a fourth aspect, the invention provides a two or multi-component system, each component of which may be in either liquid or dry form which, when combined, will provide a disinfecting solution or composition according to any one of the first, second and third aspects.

DETAILED DESCRIPTION OF PREFERRED EMBODIMENTS

The term "comprising," when used in relation to a number of integers or elements, means including without being limited to the recited integers or elements. The term "consisting essentially of" means including the recited integers or elements (and normal impurities present therein) and such additional integers or elements that do not materially affect the basic and novel properties of the invention. "Basic and novel properties of the invention" means the antimicrobial properties of the invention. The term "consisting of" means including only the recited integers or elements and no additional integers or elements, except those that may be present as normal impurities.

The expression of quantity in terms of "% w/w" means the percentage by weight, relative to the weight of the total composition, unless otherwise specified.

The term "about" when used to modify a numeric quantity of an ingredient in the compositions of the invention or employed in the methods of the invention refers to variation in the numerical quantity that can occur, for example, through typical measuring and liquid handling procedures used for making concentrates for use solutions in the real world; through inadvertent error in these procedures; through differences in the manufacture, source, or purity of the ingredients employed to make the compositions or carry out the methods; and the like. The term about also encompasses amounts that differ due to different equilibrium conditions for a composition resulting form a particular initial mixture. Whether or not modified by the term "about", the claims include equivalents to the quantities.

The singular forms, "a," "an," and "the" include plural forms unless content clearly dictates otherwise. Thus, for example, reference to a composition containing "a compound" includes a mixture of two or more compounds. It should also be noted that the term "or" is generally employed in its sense of "and/or" unless the content clearly dictates otherwise.

The terms "2-furan carboxylic acid," "2-furoic acid," and "furoic acid" are used herein interchangeably to refer to the same compound.

The present invention is intended to provide a rapid-acting hydrogen peroxide-based liquid disinfectant containing low levels of active ingredients. Some embodiments are suitable for high level disinfection. As used herein, "high level disinfection" means the destruction of *mycobacterium* species to the degree required in semicritical and critical applications, as measured by standard carrier or suspension testing methods. Also as used herein, the tend "sterilant" refers to a physical or chemical agent or process capable of destroying all forms of life (including bacteria, viruses, fungi, mycobacteria and spores) on inanimate surfaces.

Solutions according to the present invention are effective germicides, are low in toxicity and employ biodegradable ingredients. The result is a disinfectant which does not suffer from the occupational safety or environmental disposal problems associated with current technologies. Because of the low levels of hydrogen peroxide and other supplemental ingredients, "in use" solutions according to the present invention exhibit very low reactivity towards material substrates and tissue, and are therefore non or low-corrosive to skin or metals. The low hydrogen peroxide concentrations also result in improved shelf life and ease of packaging, as vented packaging would not be required.

The present invention provides solutions which are a dramatic improvement over existing hydrogen peroxide disinfectants. Contact times in high level disinfection may be reduced by factors of up to 4-5, using hydrogen peroxide concentrations which are lower by as much as one order of magnitude compared to prior art solutions.

The present solution may be used in the disinfection of semicritical and critical surfaces and/or instruments, as well as noncritical surfaces where use of an anti-tuberculosis disinfectant is recommended. Such a disinfectant is common in the dental industry and in health care settings for disinfecting respiratory equipment. A major field of application is in the processing of delicate surgical instruments and devices, including flexible endoscopes. The rather mild, non-reactive nature of the components in the mixture, and the low levels at which they are formulated, make the solution ideal for the processing of flexible medical devices, while at the same time ensuring complete disinfection, even in the presence of organic matter. The present solution may also be used to decontaminate skin.

Without being bound by theory, it is believed that the hydrogen peroxide in solutions of the present invention is central to the mechanism of disinfection. Hydrogen peroxide is believed to disrupt functions vital to the microorganism cell, for example, by inhibiting the assembly of ribosomes units within the cytoplasm of the cell. Furthermore, the decomposition of hydrogen peroxide in the solution results in the generation of hydroxyl free radicals which are believed to attack proteins and nucleic acids.

The hydrogen peroxide used in the present solution is typically a commercially available aqueous solution, usually in a concentration of 10-50% w/w. Commercial solutions for hydrogen peroxide may contain additional stabilizers and additives as are known in the art. In the present inventive solution, the preferable concentrations of hydrogen peroxide ranges from about 0.01 to about 6% w/w and more preferably from about 0.25 to about 4% w/w. While solutions with higher concentrations of hydrogen peroxide can be advantageously used, they are typically highly corrosive and have material compatibility problems. Thus, they cannot be applied in practice for the disinfection of delicate instruments. They can also be hazardous and associated with occupational safety and shipping restrictions.

It is recognized that the above specified low levels of hydrogen peroxide can be achieved by dilution of a more concentrated stock solution. Moreover, a dry particulate composition may be formulated for mixing with water by an end user to produce a solution according to the present invention. Hydrogen peroxide is commercially available in a dry form as persalt compounds, of which the preferred ones are sodium percarbonate and sodium perborate in its monohydrate and tetrahydrate forms. Since sodium percarbonate contains about 20% equivalent hydrogen peroxide by weight, and sodium perborate monohydrate and tetrahydrate contain about 30% and 20% respectively by weight, proper allowance must be made when blending the dry mixture of components to achieve the desired levels of hydrogen peroxide upon dissolution in water.

Solutions according to the present invention also contain at least one component chosen preferably from 2-furan carboxylic acid, benzoic acid, salicylic acid and benzyl alcohol, in a concentration of from 0.01 to 10% w/w, 0.01 to 8% w/w, or from 0.01 to 4% w/w of the total solution. Furan carboxylic acids are naturally occurring degradation products of lignin and cellulose. 2-furan carboxylic acid has been described as possessing some bactericidal, fungicidal and mycobactericidal activity, particularly when formulated in combination with traditional mycobactericidal ingredients. The 2-furan carboxylic acid employed in the present invention is available commercially in crystalline form, as it is typically manufactured in bulk through the Cannizaro reaction of furfural at highly alkaline conditions. It is recognized that 2-furan carboxylic acid from other sources can also be employed. For example, it may be obtained through the microbial decomposition of cellulose.

Benzyl alcohol occurs naturally in essential oils of vegetable origin. Commercially, benzyl alcohol is commonly manufactured from the reaction of benzyl chloride and sodium carbonate. Benzyl alcohol is used as a photographic developer for color movie film and in perfumes, flavour industries, pharmaceuticals as a bacteriostatic, cosmetics, ointments, emulsions, textiles, sheet plastics and inks Benzyl alcohol has a vapor pressure lower than 0.1 mm Hg (at 20° C.) which meets the standards of CARB (California Air Resources Board) for volatile organic compounds.

If inactivation of hydrophilic viruses is desired, the solution may contain at least one C6-C12 alkyl diphenyl sulfonate surfactant (e.g. alkyl diphenyl oxide disulfonate surfactant). This ingredient has been found to not only impart hydrotroping and detersive properties to the mixture, but also, surprisingly, to play a key role in the inactivation of difficult to mitigate hydrophilic viruses. The inclusion of this ingredient is believed to provide the necessary broad activity spectrum of a tuberculocidal product. Examples of this ingredient are the alkyl diphenyl oxide disulfonate surfactants manufactured commercially by the Dow Company in association with the trademark DowFax. The preferred concentration of this ingredient is from 0.05 to 3.0% w/w of the solution.

The solution may also contain from 0.005 to 3.0% w/w, from 0.01 to 3% w/w, or from 0.01 to 1% w/w of at least one non-ionic surfactant. The at least one nonionic surfactant may be chosen from (a) ethoxylated alcohols (e.g. a C6-C10 alkyl, 3.5 moles of ethylene oxide (EO) alcohol ethoxylate) and alkylglycosides having a hydrophile lyophile balance from 5 to 15; and (b) a sufficiently water-soluble block copolymer of ethylene oxide and/or propylene oxide. These ingredients impart low surface tension to the solution, improving its wetting and detergency properties. These surfactants are stable in the presence of acid hydrogen peroxide media, and do not contribute to excessive hydrogen peroxide decomposition. They are available commercially from numerous manufacturers. Examples include surfactants sold in association with (a) the trademark Alfonic by CondeaVista, (b) the trademark Tergitol by Union Carbide, and (c) the trademark Pluronic and Tetronic by BASF.

The solution may also contain at least one anionic surfactant chosen from alkali metal, alkaline earth metal, ammonium or alkylamine salts of C8-C16 alkyl benzene sulfonic acid, C8-C18 alkyl sulfonic acid, or C8-C16 alkyl ethoxylated or non ethoxylated sulfates, alkyl or alkenyl esters or diesters of sulfosuccinic acid in which the alkyl or alkenyl groups independently contain from six to eighteen carbon atoms and alkali metal, ammonium, calcium and magnesium salts thereof in a concentration of from 0.01 to 5.0% w/w of the mixture. These ingredients help impart detersive properties to the solution, and are particularly useful if the solution is used in a cleaning step prior to formal disinfection. These ingredients are available commercially from many vendors. Examples include products sold in association with the trademarks Biosoft and Stepanol by Stepan and the trademark Hostapur by Hoechst.

Other suitable anionic surfactants that can be used herein include alkyl carboxylates, salts (including, for example, sodium, potassium, ammonium, and substituted ammonium salts such as mono-, di- and triethanolamine salts) of soap, $C_8$-$C_{24}$ olefin sulfonates, sulfonated polycarboxylic acids $C_8$-$C_{24}$ alkylpolyglycolethersulfates (containing up to 10 moles of ethylene oxide); alkyl ester sulfonates such as $C_{14}$-$C_{16}$ methyl ester sulfonates; acyl glycerol sulfonates, fatty oleyl glycerol sulfates, paraffin sulfonates, alkyl phosphates, isethionates such as the acyl isethionates, alkyl succinamates, branched primary alkyl sulfates, alkyl polyethoxy carboxylates such as those of the formula RO(CH$_2$CH$_2$O)$_k$CH$_2$COO—M$^+$ wherein R is a C$_8$-C$_{22}$ alkyl, k is an integer from 0 to 10, and M is a soluble salt-forming cation. Further examples are given in "Surface Active Agents and Detergents" (Vol. I and II by Schwartz, Perry and Berch).

Chelating agents or hydrogen peroxide stabilizers may be included in the solution of the invention to enhance cleaning performance and stability of the solution. Examples include but are not limited to 1-hydroxyethylidene-1,1-diphosphonic acid sold commercially by Rhodia in association with the trademark Briquest ADPA-60AW, aminotrimethylene phosphonic acid sold commercially by Rhodia in association with the trademark Briquest 301-50A, ethylenediaminetetraacetic acid, hydroxyethylethylenediaminetriacetic acid, 2-hydroxyethyliminodiacetate (HEIDA) and nitrilotriacetic acid. Chelating agents aid the detergency process by sequestering cationic species responsible for the inactivation of anionic surfactants by cation-anion coupling, by increasing the zeta potential between substrates and soil particles, and by dissolving larger soil aggregates held together by cation bridging.

Other ingredients which are sufficiently stable in the presence of hydrogen peroxide and at the acid conditions of the present solution may be added to impart desirable qualities.

Suitable dyes and fragrances may be employed for modifying the color and odor of the solution. Thickening agents may be added to modify its rheological properties. Examples of thickening agents include but are not limited to cross-linked polyacrylates such as Carbopol™ (polymers available from Goodrich); polymeric carboxylates including modified and unmodified starches, xanthan gum, and cellulose derivatives. Corrosion inhibitors may also be added provided they are compatible with hydrogen peroxide in an acid medium and do not adversely affect the germicidal properties of the solution. Such ingredients include, but are not limited to, benzotriazoles, tolutriazoles, sodium nitrite, and sodium molybdate. Skin conditioning agents may be added to products intended for use in topical applications. Examples of skin conditioning agents include glycerin, glycerides, sorbitol, castor oil, allantoin, and polymerized quaternary ammonium compounds. Additionally, the solution may comprise an effective amount of at least one ingredient chosen from pH buffers, hydrotropes, solvents and antifoams. Antifoams can be added to the solution for low foam applications. Examples of antifoams are silicone-based antifoams such as organopolysiloxane from Dow Corning (e.g. Antifoam C and Antifoam 1410). Antifoams can also be added separately to cleaning/disinfecting machines (e.g. endoscope reprocessing machines) in which a solution according to the present invention is employed to clean or disinfect instruments or other materials in the machine.

Solutions of the present invention can be readily prepared by serial addition of the above-mentioned ingredients to deionized water. For optimum product stability, the water should have an electrical conductivity of less than 200 μS. Water purified by ion exchange or reverse osmosis is suitable for this purpose. The first ingredient(s) to be added to the required amount of water is the at least one component chosen from 2-furan carboxylic acid, benzoic acid, salicylic acid and benzyl alcohol. These ingredients are not highly soluble and therefore require more time to dissolve than the other ingredients. About 95% of the final water content of the solution is added to a mixing vessel made of high density polypropylene or passivated austenitic stainless steel, and equipped with a stirrer with shaft and blades constructed of these same materials. After addition of the at least one component and allowing sufficient time for its complete dissolution (e.g. between 0.5 to 1 hr), the rest of the ingredients can be added serially in no particular order, allowing between 30 to 45 minutes of stirring between each addition. It is preferred that the hydrogen peroxide be added as the final ingredient.

As mentioned previously, a preferred embodiment of the invention may be in dry form. In this case, one would add, in a tumbling or ribbon mixer for powdered solids, the appropriate amounts of the crystalline form of each ingredient and, optionally, a suitable crystalline filling substance such as sodium sulfate. Commercially available persalt compounds would be employed in lieu of aqueous hydrogen peroxide. Preferred examples include sodium percarbonate and sodium perborate in its monohydrate and tetrahydrate forms.

Alternatively, one can formulate a dry mixture containing all ingredients except the benzyl alcohol and hydrogen peroxide or dry hydrogen peroxide releasing components. This mixture would then be added to the benzyl alcohol and hydrogen peroxide in aqueous or dry form at the moment of use. This application is useful when using automatic machines that are equipped for dosing and mixing two-part systems.

As mentioned above, the present solutions are suitable for the disinfection of delicate and chemically sensitive materials with minimal occupational safety risks. Some embodiments of the present invention are particularly useful in the disinfection of semicritical and critical surfaces and instruments in the health care, veterinary care and dental care industries. Specific applications include, but are not limited to, the cleaning and disinfection of invasive and non-invasive surgical equipment, the cleaning and disinfection of rigid and flexible invasive and non-invasive diagnostic equipment, the cleaning and disinfection of prostheses and implants, the internal cleaning and disinfection of body fluids recirculating machinery, the cleaning and disinfection of noncritical surfaces where the use of products with tuberculocidal efficacy is recommended, such as dental chairs and respiratory resuscitation equipment, and topical applications such as skin disinfection.

The methods of application of the present disinfecting solution include, but are not limited to, spraying the solution on the surface to be treated with a spraying trigger or nozzle, simply wetting the area or instrument with the solution, filling an enclosed space (a tube for example) with the solution and allowing the solution to sit there for the required contact time, and circulating the solution in place through internal conduits and passages of an instrument or equipment to be disinfected for a predetermined period of time. The solution can be applied at room temperature or at another temperature (i.e. from 4° C. to as high as 70° C., or from 20 to 60° C.).

When the present invention is prepared as a dry mixture, the above mentioned application methods can still be used; however, the dry mixture must first be dissolved in water to produce the present aqueous solution. Preparation of the present aqueous solution may be done in situ or just prior to use, either manually or automatically in a washing disinfection machine equipped for handling powders.

EXAMPLES

The following examples are intended simply to illustrate embodiments of solutions according to the present invention and should not be regarded as narrowing in scope. One skilled in the art will readily recognize that these examples suggest many other ways in which the present invention could be practised.

Embodiments of the present invention were formulated using ingredients, including the following ingredients.

Phosphorous-Based Compounds and/or Cation Sequestering Agents
   $H_3PO_4$=phosphoric acid (used to buffer solution to the desired pH)
   Briquest ADPA-60AW (HEDP)=1-hydroxyethylidene-1,1,-diphosphonic acid sold by Rhodia as a 60% w/w solution (this ingredient serves to stabilize the hydrogen peroxide in solution)
   Briquest ADPA-60SH=sodium salt of 1-hydroxyethylidene-1,1,-diphosphonic acid sold by Rhodia as a 60% w/w powder
Anionic Surfactants/Hydrotropes
   Biosoft S-100 (DDBSA)=dodecyl benzene sulfonic acid manufactured by Stepan as a 98% w/w solution
   Dowfax C10L=C10 alkylated sulfonated diphenyl oxide disodium salt manufactured by the Dow Chemical Company as a 45 w/w solution
   C6 Dowfax hydrotrope=C6 alkylated sulfonated diphenyl oxide disodium salt manufactured by the Dow Chemical Company as a 40% w/w solution
   Aerosol OT-75=sodium dioctyl sulfosuccinate manufactured by Cytec as a 75% w/w solution
   Stepanate SXS=☐sodium xylene sulfonate, manufactured by Stepan as a 40% w/w solution
   Bioterge PAS 8S=sodium octyl sulfonate manufactured by Stepan as a 40% w/w solution
Non-Ionic Surfactants (Emulsifiers)
   Alfonic L610-3.5=100% w/w active C6-C10 alkyl, 3.5 moles of ethylene oxide (EO) alcohol ethoxylate (AE) manufactured by Sasol (this is an alcohol-based non-ionic surfactant, ethoxylated to an average of 3.5 moles of ethylene oxide per mole of alcohol)
   Ethal OA-23: oleyl ($C_{18}$) alcohol ethoxylate, 23 moles of EO/mole of alcohol, manufactured or sold by Ethox Company as a 70% w/w solution
Corrosion Inhibitors
   Cobratec 35-G=1,2,3 benzotriazole manufactured by PMC Specialties Group as a 35 w/w solution
   sodium molybdate
   Cobratec 99=a 99% w/w active dehydrated 1,2,3 benzotriazole, manufactured by PMC Specialties Group
   sodium nitrite
Additional Buffers (for Achieving Desired pH)
   citric acid
   lactic acid
   NaOH=sodium hydroxide
   KOH=potassium hydroxide
   $CaCO_3$=calcium carbonate
   $Na_2CO_3$=sodium carbonate
Thickening Agents
   Keltrol T630=xanthan gum (polysaccharide) manufactured or sold by Pkelco Company
   Natrosol 250H NF=hydroxyethylcellulose, manufactured or sold by Hercules Incorporated
Conditioning Agents:
   Glycerin
   Sorbitol
Antifoam
   Antifoam C=polydimethylsiloxane from Dow Corning
Test Methods and Organisms
   Tests were conducted using the following test organisms: *Pseudomonas aeruginosa* (ATCC 15442), *Staphylococcus aureus* (ATCC 6538), *Salmonella choleraesuis* (ATCC 10708), *Mycobacterium terrae* (ATCC 15755), *Trichophyton mentagrophytes* (ATCC 9533), the Sabin vaccine strain of polio virus type 1 (ATCC VR-192), spores of *bacillus subtilis* (ATCC 19659) were used, and a seed culture of *Acinetobacter baumannii*.

Solutions were tested using ASTM E2111 (Standard Quantitative Carrier Test Method To Evaluate the Bactericidal, Fungicidal, Mycobactericidal and Sporicidal Potencies of Liquid Chemical Geiuiicides, ASTM International, 2000), ASTM E2197 (Standard Quantitative Disk Carrier Test Method for Determining the Bactericidal, Virucidal, Fungicidal, Mycobactericidal and Sporicidal Activities of Liquid Chemical Germicides, ASTM International, 2002), and ASTM E1053/97 (Standard Test Method for Efficacy of Virucidal Agents Intended for Inanimate Environmental Surfaces, ASTM International, 2002).

Experimental Data

Compositions I and II were prepared by the methods described herein as per the tables below.

| Composition I | | |
| --- | --- | --- |
| Ingredient | % w/w whole basis | % w/w active basis (active concentration in solution) |
| hydrogen peroxide (50%) | 1.00 | 0.50 |
| 2-furan carboxylic acid (97%) | 0.50 | 0.48 |
| Dowfax C10L (45%) | 0.18 | 0.08 |
| Alfonic L610-3.5 (100%) | 0.05 | 0.05 |
| phosphoric acid (75%) | 2.00 | 1.50 |
| Biosoft S-100 (98%) | 0.18 | 0.176 |
| Briquest ADPA-60AW (60%) | 0.50 | 0.30 |
| deionized water | 94.59 | 96.908 |
| pH | 1.8 | 1.8 |

Composition I is particularly useful as a hard surface cleaner.

| Composition II | | |
| --- | --- | --- |
| Ingredient | % w/w whole basis | % w/w active basis (active concentration in solution) |
| hydrogen peroxide (50%) | 1.50 | 0.75 |
| 2-furan carboxylic acid (99%) | 0.38 | 0.376 |
| Cobratec 99 (99%) | 0.12 | 0.119 |
| Sodium molybdate (100%) | 0.015 | 0.015 |
| Sodium nitrite (100%) | 0.015 | 0.015 |
| Sodium carbonate (100%) | 0.09 | 0.09 |
| tap water | 96.90 | 98.635 |
| pH | 4.0 | 4.0 |

All components of Composition II, with the exception of the hydrogen peroxide, were mixed as dry powders to form a dry powdered mixture. Then, prior to use, this powdered mixture and the required amount of aqueous hydrogen peroxide were added to the appropriate amount of tap water.

Example I

Composition I was tested for its effectiveness as a sanitizer and also for its bactericidal, virucidal, fungicidal and mycobactericidal activity using a variety of test methodologies.

Table 1 below summarizes the results of tests against *Staphylococcus aureus*. All three trials were able to bring about a >7 $\log_{10}$ reduction in the viability titre of *S. aureus* in a contact time of 5 minutes at room temperature indicating bactericidal activity against this organism.

TABLE 1

The activity of Composition I against *Staphylococcus aureus* (ASTM E2111)

| Trial | Contact Time (minutes) | CFU/Control Carrier | Average CFU Test Carrier | $\text{Log}_{10}$ Reduction |
|---|---|---|---|---|
| 1 | 5 | $1.11 \times 10^7$ | 0 | 7.74 |
| 2 | 5 | $1.11 \times 10^7$ | 0 | 7.74 |
| 3 | 5 | $1.11 \times 10^7$ | 0 | 7.74 |

Table 2 below summarizes the results of tests against *Pseudomonas aeruginosa*. All three trials were able to bring about a >6 $\log_{10}$ reduction in the viability titre of *P. aeruginosa* in a contact time of 5 minutes at room temperature indicating bactericidal activity against this organism.

TABLE 2

The activity of Composition I against *Pseudomonas aeruginosa* (ASTM E2111)

| Trial | Contact Time (minutes) | CFU/Control Carrier | Average CFU Test Carrier | $\text{Log}_{10}$ Reduction |
|---|---|---|---|---|
| 1 | 5 | $2.04 \times 10^6$ | 0 | 6.31 |
| 2 | 5 | $2.04 \times 10^6$ | 0 | 6.31 |
| 3 | 5 | $2.04 \times 10^6$ | 0 | 6.31 |

Table 3 below summarizes the results of tests against *Salmonella choleraesuis*. All three trials were able to bring about a >6 $\log_{10}$ reduction in the viability titre of *S. choleraesuis* in a contact time of 5 minutes at room temperature indicating bactericidal activity against this organism.

TABLE 3

The activity of Composition I against *Salmonella choleraesuis* (ASTM E2111)

| Trial | Contact Time (minutes) | CFU/Control Carrier | Average CFU Test Carrier | $\text{Log}_{10}$ Reduction |
|---|---|---|---|---|
| 1 | 5 | $2.26 \times 10^6$ | 0 | 6.34 |
| 2 | 5 | $1.17 \times 10^6$ | 0 | 6.07 |
| 3 | 5 | $1.17 \times 10^6$ | 0 | 6.07 |

Table 4 below summarizes the results of tests *Acinetobacter baumannii*. All three trials were able to bring about a >6-$\log_{10}$ reduction in the viability titre of *Acinetobacter baumannii* in a contact time of 5 minutes at room temperature indicating bactericidal activity against this organism.

TABLE 4

The activity of Composition I against *Acinetobacter baumannii* (ASTM E2111)

| Trial | Contact Time (minutes) | CFU/Control Carrier | Average CFU Test Carrier | $\text{Log}_{10}$ Reduction |
|---|---|---|---|---|
| 1 | 5 | $1.02 \times 10^6$ | 0 | 6.00 |
| 2 | 5 | $1.71 \times 10^6$ | 0 | 6.23 |
| 3 | 5 | $1.71 \times 10^6$ | 0 | 6.23 |

Table 5 below summarizes the results of tests against *Mycobacterium terrae*. All three trials were able to bring about a >5-$\log_{10}$ reduction in the viability titre of *M. terrae* in a contact time of 5 minutes at room temperature indicating bactericidal activity against this organism.

TABLE 5

The activity of Composition I against *Mycobacterium terrae* (ASTM E2111)

| Trials | Contact Time (minutes) | CFU/Control Carrier | Average CFU Test Carrier | $\text{Log}_{10}$ Reduction |
|---|---|---|---|---|
| 1 | 5 | $2.0 \times 10^5$ | 0 | 5.30 |
| 2 | 5 | $2.0 \times 10^5$ | 0 | 5.30 |
| 3 | 5 | $2.0 \times 10^5$ | 0 | 5.30 |

Table 6 below summarizes the results of tests against *Trichophyton mentagrophytes*. All three trials were able to bring about a >5-$\log_{10}$ reduction in the viability titre of *T. mentagrophytes* in a contact time of 5 minutes at room temperature indicating bactericidal activity against this organism.

TABLE 6

The activity of Composition I against *Trichophyton mentagrophytes* (ASTM E2111)

| Trials | Contact Time (minutes) | CFU/Control Carrier | Average CFU Test Carrier | $\text{Log}_{10}$ Reduction |
|---|---|---|---|---|
| 1 | 5 | $1.13 \times 10^5$ | 0 | 5.05 |
| 2 | 5 | $1.13 \times 10^5$ | 0 | 5.05 |
| 3 | 5 | $1.13 \times 10^5$ | 0 | 5.05 |

Table 7 below summarizes the results of tests against Sabin vaccine strain of poliovirus type 1. All three trials were able to bring about a >4 $\log_{10}$ reduction in the viability titre of the polio virus in a contact time of 5 minutes at 20±1° C., indicating virucidal activity against this organism.

TABLE 7

The activity of Composition I against Poliovirus type 1 (Sabin) (ASTM E2197)

| Trials | Contact Time (minutes) | PFU/Control Carrier | Average PFU Test Carrier | $\text{Log}_{10}$ Reduction |
|---|---|---|---|---|
| 1 | 5 | $1.28 \times 10^4$ | 0 | 4.10 |
| 2 | 5 | $1.28 \times 10^4$ | 0 | 4.10 |
| 3 | 5 | $8.00 \times 10^4$ | 0 | 4.70 |

Example II

This example further illustrates the mycobactericidal activity of Composition I, as well as the synergy of the 2-furan carboxylic acid and hydrogen peroxide in the mixture. The methodology employed for the evaluation of mycobactericidal efficacy is the quantitative carrier method (ASTM E2111). Currently, the passing standard in Canada for non-critical disinfection is a greater than 4-$\log_{10}$ reduction in viable numbers of microorganisms, while for semicritical and critical applications it is a greater than 6-$\log_{10}$ reduction.

The results for Composition I and alternative compositions A, B, and C are tabled below.

TABLE II

| TEST SAMPLE | $\text{Log}_{10}$ reduction |
|---|---|
| Composition I | 5.30 in 5 min. |
| (A) 0.50% 2-furoic acid in DI water at a pH of 1.8 | <2.0 in 5 min. |
| (B) 0.50% hydrogen peroxide in DI water at a pH of 1.8 | <1.0 in 5 min. |
| (C) Composition I without 2-furoic acid | <1.0 in 5 min. |

DI water = deionized water

It is seen from the above results that there is a clear, unexpected synergy between the 2-furoic acid and one or more of the other components of Composition I, as a simple additive effect would yield a $\log_{10}$ reduction of less than $4.0 \log_{10}$.

Example III

In this example, the sporicidal and mycobactericidal properties of Composition II are illustrated. Once again, the quantitative carrier test method ASTM E2111 was used. However, the experiments were run at a temperature of 54° C. to simulate use of the disinfectant in an endoscope processing machine. The surrogate organism for measuring sporicidal efficacy was *Bacillus subtilis*. The surrogate organism for measuring mycobactericidal efficacy was *mycobacterium terrae*. Once more, relevant comparative examples (Compositions A, B, and C) are included which describe the synergy between the 2-furoic acid and other components of the solution. The contact time was 15 minutes.

TABLE III

| TEST SAMPLE | $\log_{10}$ reduction (bacillus subtilis) | $\log_{10}$ reduction (mycobacterium terrae) |
|---|---|---|
| Composition II | 6.04 | 7.00 |
| (A) Composition II with 0.50% active hydrogen peroxide and no 2-furoic acid | 4.60 | |
| (B) Composition II with no 2-furoic acid | 4.90 | |
| (C) Composition II with 0.75% 2-furoic acid and no H2O2 | <<4.0 | |

It is seen from the above results that the addition of a small amount of 2-furoic acid to a 0.75% active hydrogen peroxide solution (Composition II) will increase the efficacy of the solution by more than 1 order of magnitude in relation to 0.75% hydrogen peroxide alone (Composition B), and by more than 2 orders of magnitude with respect to a 2-furoic acid based solution (Composition C).

Example IV

Composition I was evaluated for its acute skin and eye irritation, as well as oral toxicity. The standard methods for testing chemicals established by the OECD (standards OECD Sec. 404, 405, 420, respectively) were used and the results are summarized below.

| TEST SAMPLE | Acute eye irritation class | Acute skin irritation | Oral $LD_{50}$ |
|---|---|---|---|
| Composition I | Minimally irritating | Irritation index 0.50 | >2000 mg/Kg |

In parallel testing of skin irritation with a commercial surgical soap based on chloroxylenol, it was found that the hand soap, in spite of containing a variety of ingredients to minimize skin irritation and promote moisturizing, scored a much higher irritation index of 2.25. An acute skin irritation index score between 0.01 and 1.99 classifies a substance as a slight irritant, while a score of 2.00-5.00 means that the substance is a moderate irritant. Furthermore, an oral $LD_{50}$ score of over 2000 mg/Kg means that the substance is classified as nontoxic when ingested.

Example V

Composition I was subjected to an accelerated hot stability test in order to evaluate hydrogen peroxide stability in the solution. A sample was subjected to a temperature of 50° C. for 1 week and the hydrogen peroxide content was measured by iodometric titration before and after the test. The observed loss of hydrogen peroxide was 3.41% of the initial concentration which indicates that, in practice, the solution would have a room temperature shelf life in excess of 1 year.

Example VI

Solutions A, B, C, D and E were prepared in accordance with Table VIa below and their activities against various organisms are summarized in Tables VIb, VIc and VId below.

TABLE VIa

| Ingredient | A % w/w | B % w/w | C % w/w | D % w/w | E % w/w |
|---|---|---|---|---|---|
| Deionized water | Up to 100 | Up to 100 | Up to 100 | Up to 100 | Up to 100 |
| Phosphoric acid (75%) | 0.15 | 0.15 | 0.15 | 0.15 | 0.15 |
| | 0.11 | 0.11 | 0.11 | 0.11 | 0.11 |
| Briquest ADPA-60AW (60%) | 0.48 | 0.48 | 0.48 | 0.48 | 0.48 |
| | 0.29 | 0.29 | 0.29 | 0.29 | 0.29 |
| C6 Dowfax hydrotrope (40%) | 0.18 | 0.18 | 0.18 | 0.18 | 0.18 |
| | 0.07 | 0.07 | 0.07 | 0.07 | 0.07 |
| Biosoft S-100 (98%) | 0.18 | 0.18 | 0.18 | 0.18 | 0.18 |
| | 0.18 | 0.18 | 0.18 | 0.18 | 0.18 |
| Alfonic L610-3.5 (100%) | 0.05 | 0.05 | 0.05 | 0.05 | 0.05 |
| | 0.05 | 0.05 | 0.05 | 0.05 | 0.05 |
| Hydrogen peroxide (50%) | 1.10 | 1.10 | 1.10 | 1.10 | 1.10 |
| | 0.55 | 0.55 | 0.55 | 0.55 | 0.55 |
| Benzyl alcohol (99%) | 2.50 | 2.50 | 2.50 | 2.50 | 0 |
| | 2.50 | 2.50 | 2.50 | 2.50 | 0 |
| pH (adjust with effective amount of NaOH) | 1.8 | 2.4 | 3.0 | 4.0 | 1.8 |

The active concentration in solution is shown in bold in the second row corresponding to each ingredient.

TABLE VIb

The activity of Solutions A-E against *M. terrae* (ASTM E2111)

| Solution | Contact Temp | Contact Time | CFU/control Carrier | CFU/test Carrier | $\log_{10}$ Red'n |
|---|---|---|---|---|---|
| A | RT | 5 min | $1.83 \times 10^6$ | 0 | 6.26 |
| B | RT | 5 min | $1.83 \times 10^6$ | 0 | 6.26 |
| C | RT | 5 min | $1.83 \times 10^6$ | 0 | 6.26 |
| D | RT | 5 min | $1.83 \times 10^6$ | 2 | 6.03 |
| E | RT | 5 min | $1.83 \times 10^6$ | TNTC | * |

TNTC: too numerous to count (means there is no activity)
RT = room temperature

TABLE VIc

The activity of Solutions A-E against *T. mentagrophytes* (ASTM E2111)

| Solution | Contact Temp | Contact Time | CFU/control Carrier | CFU/test Carrier | $\log_{10}$ Red'n |
|---|---|---|---|---|---|
| A | RT | 5 min | $2.53 \times 10^5$ | 0 | 5.4 |
| B | RT | 5 min | $2.17 \times 10^5$ | 0 | 5.3 |
| C | RT | 5 min | $2.17 \times 10^5$ | 2 | 5.21 |
| D | RT | 5 min | $2.17 \times 10^5$ | 5 | 4.7 |
| E | RT | 5 min | $2.17 \times 10^5$ | TNTC | * |

TNTC: too numerous to count (means there is no activity)
RT = room temperature

TABLE VId

The activity of Solutions A-E against *Staphylococcus aureus* (ASTM E2111)

| Solution | Contact Temp | Contact Time | CFU/control Carrier | CFU/test Carrier | $Log_{10}$ Red'n |
|---|---|---|---|---|---|
| A | RT | 5 minutes | $6.67 \times 10^6$ | 0 | 6.82 |
| B | RT | 5 minutes | $6.67 \times 10^6$ | 0 | 6.82 |
| C | RT | 5 minutes | $6.67 \times 10^6$ | 0 | 6.82 |
| D | RT | 5 minutes | $6.67 \times 10^6$ | 0 | 6.82 |
| E | RT | 5 minutes | $1.66 \times 10^6$ | 0 | 6.22 |

RT = room temperature

Solution B was evaluated for its acute skin and eye irritation in accordance with OECD standards section 404 and 405. The results are summarized in Table VIe below.

TABLE VIe

| | Acute skin irritation | Acute eye irritation class |
|---|---|---|
| Solution B | Irritation index 0.0 | Non irritating |

Example VII

Solution F was prepared in accordance with Table VIIa below and its activity against *T. mentagrophytes* is summarized in Table VIIb below.

TABLE VIIa

| Ingredient | F % w/w |
|---|---|
| Deionized water | Up to 100 |
| Phosphoric acid (75%) | 0.15 |
| | 0.11 |
| Briquest ADPA-60AW (60%) | 0.48 |
| | 0.29 |
| C6 Dowfax hydrotrope (40%) | 0.18 |
| | 0.07 |
| Biosoft S-100 (98%) | 0.18 |
| | 0.18 |
| Alfonic L610-3.5 (100%) | 0.05 |
| | 0.05 |
| Hydrogen peroxide (50%) | 1.10 |
| | 0.55 |
| Benzyl alcohol (99%) | 1.50 |
| | 1.50 |
| pH (adjust with effective amount of NaOH) | 1.8 |

The active concentration in solution is shown in bold in the second row corresponding to each ingredient.

TABLE VIIb

The activity of Solution F against *T. mentagrophytes* (ASTM E2111)

| Solution | Contact Temp | Contact Time | CFU/control Carrier | CFU/test Carrier | $Log_{10}$ Red'n |
|---|---|---|---|---|---|
| F | RT | 5 min | $3.8 \times 10^5$ | 0 | 5.58 |

RT = room temperature

Example VIII

Solutions G, H and I were prepared in accordance with Table VIIIa below and their activities against various organisms are summarized in Tables VIIIb, VIIIc, VIIId and VIIIe below.

TABLE VIIIa

| Ingredient | G % w/w | H % w/w | I % w/w |
|---|---|---|---|
| Deionized water | To 100 | To 100 | To 100 |
| Briquest ADPA-60AW (60%) | 0.50 | 0.50 | 0.50 |
| | 0.30 | 0.30 | 0.30 |
| Dowfax C10L (45%) | 0.19 | 0.19 | 0.19 |
| | 0.09 | 0.09 | 0.09 |
| Biosoft S-100 (98%) | 0.18 | 0.18 | 0.18 |
| | 0.18 | 0.18 | 0.18 |
| Alfonic L610-3.5 (100%) | 0.05 | 0.05 | 0.05 |
| | 0.05 | 0.05 | 0.05 |
| Citric acid (99%) | 0.50 | 0.50 | 0.50 |
| | 0.50 | 0.50 | 0.50 |
| Phosphoric acid (75%) | 2.00 | 2.00 | 2.00 |
| | 1.50 | 1.50 | 1.50 |
| Hydrogen peroxide (50%) | 4.00 | 3.60 | 4.00 |
| | 2.00 | 2.00 | 2.00 |
| Sodium molybdate (99%) | 0.01 | 0.01 | 0.01 |
| | 0.01 | 0.01 | 0.01 |
| Cobratec 35-G (35% benzotriazole) | 0.50 | 0.50 | 0.50 |
| | 0.18 | 0.18 | 0.18 |
| Benzyl alcohol (99%) | 2.40 | 2.00 | 2.00 |
| | 2.38 | 1.98 | 1.98 |
| NaOH | Up to pH = 4.0 | Up to pH = 4.0 | Up to pH = 5.0 |

The active concentration in solution is shown in bold in the second row corresponding to each ingredient.

TABLE VIIIb

The activity of Solutions G, H and I against *M. terrae* (ASTM E2111)

| Solution | Contact Temp | Contact Time | CFU/control Carrier | CFU/test Carrier | $Log_{10}$ Red'n |
|---|---|---|---|---|---|
| G | RT | 15 min | $8.3 \times 10^6$ | 0 | 6.92 |
| H | RT | 15 min | $8.3 \times 10^6$ | 0 | 6.92 |
| I | RT | 15 min | $8.3 \times 10^6$ | 0 | 6.92 |

RT = room temperature

TABLE VIIIc

The activity of Solutions G, H and I against *T. mentagrophytes* (ASTM E2111)

| Solution | Contact Temp | Contact Time | CFU/control Carrier | CFU/test Carrier | $Log_{10}$ Red'n |
|---|---|---|---|---|---|
| G | RT | 15 min | $2.7 \times 10^5$ | 0 | 5.43 |
| H | RT | 15 min | $2.7 \times 10^5$ | 0 | 5.43 |
| I | RT | 15 min | $2.7 \times 10^5$ | 0 | 5.43 |

RT = room temperature

TABLE VIIId

The activity of Solutions G, H and I against Polio virus (ASTM E1053(97))

| Solution | Contact Temp | Contact Time | CFU/control Carrier | CFU/test Carrier | $Log_{10}$ Red'n |
|---|---|---|---|---|---|
| G | RT | 15 min | $6.87 \times 10^4$ | 0 | 4.84 |
| H | RT | 15 min | $6.87 \times 10^4$ | 0 | 4.84 |
| I | RT | 15 min | $6.87 \times 10^4$ | 0 | 4.84 |

RT = room temperature

TABLE VIIIe

The activity of Solutions G and H against *B. subtilis* (ASTM E2111)

| Solution | Contact Temp | Contact Time | CFU/control Carrier | CFU/test Carrier | Log$_{10}$ Red'n |
|---|---|---|---|---|---|
| G | RT | 6 hrs | $8.43 \times 10^6$ | 0 | 6.92 |
| H | RT | 6 hrs | $8.43 \times 10^6$ | 0 | 6.92 |

RT = room temperature

Example IX

Solutions J, K, L and M were prepared in accordance with Table IXa below and their activities against *M. terrae* are summarized in Table IXb below.

TABLE IXa

| Ingredient | J % w/w | K % w/w | L % w/w | M % w/w |
|---|---|---|---|---|
| Deionized water | To 100 | To 100 | To 100 | To 100 |
| Briquest ADPA-60AW (60%) | 1.0 | 1.0 | 1.0 | 1.0 |
|  | 0.60 | 0.60 | 0.60 | 0.60 |
| Dowfax C10L (45%) | 0.19 | 0.09 | 0.19 | 0.19 |
|  | 0.09 | 0.09 | 0.09 | 0.09 |
| Biosoft S-100 (98%) | 0.18 | 0.18 | 0.18 | 0.18 |
|  | 0.18 | 0.18 | 0.18 | 0.18 |
| Alfonic L610-3.5 (100%) | 0.05 | 0.05 | 0.05 | 0.05 |
|  | 0.05 | 0.05 | 0.05 | 0.05 |
| Phosphoric acid (75%) | 2.00 | 2.00 | 2.00 | 2.00 |
|  | 1.50 | 1.50 | 1.50 | 1.50 |
| Hydrogen peroxide (50%) | 4.00 | 4.00 | 4.00 | 4.00 |
|  | 2.00 | 2.00 | 2.00 | 2.00 |
| Sodium molybdate (99%) | 0.01 | 0.01 | 0.01 | 0.01 |
|  | 0.01 | 0.01 | 0.01 | 0.01 |
| Cobratec 35-G (35% benzotriazole) | 0.50 | 0.50 | 0.50 | 0.50 |
|  | 0.18 | 0.18 | 0.18 | 0.18 |
| 2-Furoic acid (99%) | 1.0 | 0.5 | 2.7 | 2.7 |
|  | 0.99 | 0.50 | 2.67 | 2.67 |
| Benzyl alcohol (99%) | 0 | 0 | 0 | 2.0 |
|  | 0 | 0 | 0 | 1.98 |
| NaOH | Up to pH = 3.0 | Up to pH = 3.0 | Up to pH = 4.0 | Up to pH = 4.0 |

The active concentration in solution is shown in bold in the second row corresponding to each ingredient.

TABLE IXb

The activity of Solutions J, K, L, and M against *M. terrae* (ASTM E2111)

| Solution | Contact Temp | Contact Time | CFU/control Carrier | CFU/test Carrier | Log$_{10}$ Red'n |
|---|---|---|---|---|---|
| J | RT | 15 min | $1.06 \times 10^7$ | 0 | 7.02 |
| K | RT | 15 min | $1.06 \times 10^7$ | 46 | 5.4 |
| L | RT | 15 min | $1.24 \times 10^7$ | 1 | 7.09 |
| M | RT | 15 min | $9.33 \times 10^6$ | 0 | 6.77 |

RT = room temperature

Example X

Solutions P and Q were prepared in accordance with Table Xa and Xb below and their activities against *B. subtilis* are summarized in Table Xc.

TABLE Xa

| Ingredient | N % w/w | O % w/w |
|---|---|---|
| Deionized water | To 100 | To 100 |
| Briquest ADPA-60AW (60%) | 3.0 | 3.0 |
|  | 1.80 | 1.80 |
| Stepanate SXS (40%) | 10 | 10 |
|  | 4.00 | 4.00 |
| Propylene glycol (99%) | 10 | 10 |
|  | 9.90 | 9.90 |
| Sodium molybdate (99%) | 0.5 | 0.5 |
|  | 0.50 | 0.50 |
| Cobratec 35-G (35% benzotriazole) | 15.0 | 15.0 |
|  | 5.25 | 5.25 |
| 2-Furoic acid (99%) | 10.0 | 10.0 |
|  | 9.90 | 9.90 |
| Citric acid (99%) | 1.0 | 1.0 |
|  | 1.00 | 1.00 |
| Benzyl alcohol (99%) | 10 | 10 |
|  | 9.90 | 9.90 |
| NaOH | Up to pH = 4.0 | Up to pH = 4.0 |

The active concentration in solution is shown in bold in the second row corresponding to each ingredient.

TABLE Xb

| Ingredient | P % w/w | Q % w/w |
|---|---|---|
| Formulation N | 4 | 0 |
| Formulation O | 0 | 4 |
| Hydrogen peroxide (50%) | 3 | 3 |
| Water (200 ppm hardness) | To 100 | To 100 |

TABLE Xc

The activity of Solutions P and Q against *B. subtilis* (ASTM E2111)

| Solution | Contact Temp | Contact Time | CFU/control Carrier | CFU/test Carrier | $Log_{10}$ Red'n |
|---|---|---|---|---|---|
| P | 54° C. | 15 min | $1.08 \times 10^7$ | 20 | 6.13 |
| Q | 54° C. | 15 min | $1.08 \times 10^7$ | 1 | 6.91 |

Example XI

Solutions R and S were prepared in accordance with Table XIa below and their activities against a selected organism are summarized in Table XIb and XIc below.

TABLE XIa

| Ingredient | R % w/w | S % w/w |
|---|---|---|
| Deionized water | To 100 | To 100 |
| Briquest ADPA-60AW (60%) | 0.12 | 0.12 |
|  | 0.07 | 0.07 |
| Sodium molybdate (99%) | 0.02 | 0.02 |
|  | 0.02 | 0.02 |
| Cobratec 99 (99% benzotriazole) | 0.3 | 0.3 |
|  | 0.30 | 0.30 |
| 2-Furoic acid (99%) | 0.4 | 0.05 |
|  | 0.40 | 0.40 |
| hydrogen peroxide (50%) | 0.75 | 0.25 |
|  | 0.40 | 0.12 |
| CaCO3 or KOH | Up to pH = 6.0 | Up to pH = 4.0 |

The active concentration in solution is shown in bold in the second row corresponding to each ingredient.

TABLE XIb

The activity of Solution R against *B. subtilis* (ASTM E2111)

| Solution | Contact Temp | Contact Time | CFU/control Carrier | CFU/test Carrier | $Log_{10}$ Red'n |
|---|---|---|---|---|---|
| R | 54° C. | 15 min | $1.3 \times 10^6$ | 0 | 6.11 |

TABLE XIc

The activity of Solution S against *M. terrae* (ASTM E2111)

| Solution | Contact Temp | Contact Time | CFU/control Carrier | CFU/test Carrier | $Log_{10}$ Red'n |
|---|---|---|---|---|---|
| S | 54° C. | 10 min | $4.26 \times 10^6$ | 0 | 6.62 |

Example XIIa

A multi-part system according to a further embodiment of the invention, comprising Solution S1 (summarized in Table XII below), can be made by mixing one part of Solution S1, 2 parts of hydrogen peroxide (50% solution), and 97 parts of water to provide a disinfecting solution that can be used at 40-60° C. in high level disinfection. The pH of the mixture should be adjusted to about 3 by adding a suitable pH adjuster (e.g. phosphoric acid or potassium hydroxide) to the solution before disinfection.

TABLE XII

| Ingredient | S1 % w/w |
|---|---|
| Deionized water | To 100 |
| Stepanate SXS (40%) | 8 |
|  | 3.2 |
| Propylene glycol (99%) | 8 |
|  | 8 |
| Sodium molybdate (99%) | 0.5 |
|  | 0.50 |
| Cobratec 35-G (35% benzotriazole) | 3 |
|  | 1.05 |
| 2-Furoic acid (99%) | 20 |
|  | 19.8 |
| Glycolic acid (60%) | 10 |
|  | 6 |
| KOH | Up to pH = 6.0 |

The active concentration in solution is shown in bold in the second row corresponding to each ingredient.

Example XIIb

A dry powdered mixture in accordance with a further embodiment (Composition S2) can be prepared by mixing together 4 parts 2-furoic acid, 2 parts sodium percarbonate, 2 parts Briquest ADPA-60SH, 0.5 part of sodium carbonate, 0.5 part of sodium molybdate, 0.5 part of citric acid, and 0.5 part of Cobratec 99. 1 part Composition S2 can be diluted with 99 parts water, and its pH adjusted to about 4 with the addition of a suitable pH adjuster (e.g. phosphoric acid or potassium hydroxide) to provide a solution that can be used as a high level disinfectant at 40-60° C.

Example XIII

Solution T was prepared in accordance with Table XIIIa below and its activity against *M. terrae* is summarized in Table XIIIb below.

TABLE XIIIa

| Ingredient | T % w/w |
|---|---|
| Deionized water | Up to 100 |
| Phosphoric acid (75%) | 0.15 |
|  | 0.11 |
| Briquest ADPA-60AW (60%) | 0.48 |
|  | 0.29 |
| C6 Dowfax hydrotrope (40%) | 0.18 |
|  | 0.07 |
| Biosoft S-100 (98%) | 0.18 |
|  | 0.18 |
| Alfonic L610-3.5 (100%) | 0.05 |
|  | 0.05 |
| Hydrogen peroxide (50%) | 1.10 |
|  | 0.55 |
| Benzyl alcohol (99%) | 3.0 |
|  | 3.00 |
| pH adjusted using effective amount of NaOH buffer | 2.4 |

The active concentration in solution is shown in bold in the second row corresponding to each ingredient.

TABLE XIIIb

The activity of Solution T against *M. terrae* (ASTM E2111)

| Solution | Contact Temp | Contact Time | CFU/control Carrier | CFU/test Carrier | $Log_{10}$ Red'n |
|---|---|---|---|---|---|
| T | RT | 1 min | $8.4 \times 10^6$ | 3 | 6.56 |

RT = room temperature

In the above examples, Solutions A, B, C, D, E, F, and T are hard surface disinfectants. Solutions G, H, I, J, K, L, M are high level disinfectants and sterilants and can also be used as hard surface cleaners. Solutions N, O, P, Q, R, and S are high level disinfectants and chemosterilants and can also be used to disinfect medical and other devices.

Example XIV

Additional solutions according to various embodiments of the invention are summarized in Table XIV below.

TABLE XIV

| Ingredient | U % w/w | V % w/w | W % w/w | X % w/w | Y % w/w | Z % w/w | Z1 % w/w |
|---|---|---|---|---|---|---|---|
| Deionized water | Qs to 100 | Qs to 100 | Qs to 100 | Qs to 100 | Qs to 100 | Qs to 100 | Qs to 100 |
| Natrosol 250H NF | 0.2 | 0 | 0.25 | 0 | 0 | 0 | 0 |
| Keltrol T630 | 0 | 0.2 | 0.25 | 0.5 | 0 | 0 | 0 |
| Biosoft S-100 (DDBSA) | 0.1 | 0.2 | 0.05 | 0.15 | 0.18 | 0.18 | 0 |
| Dowfax C10L | 0 | 0 | 0 | 0.1 | 0.18 | 0.18 | 0 |
| Aerosol OT-75 | 0.05 | 0 | 0.1 | 0.2 | 0 | 0 | 0.2 |
| Ethal OA-23 | 0 | 0 | 0 | 0 | 0.05 | 0.05 | 0.05 |
| Lactic acid | 0.30 | 0 | 0.25 | 0 | 0 | 0 | 0 |
| Citric acid | 0 | 0.5 | 0 | 0.2 | 0.5 | 0.5 | 0.5 |
| Phosphoric acid | 0 | 0.1 | 0 | 0.1 | 0.4 | 0.4 | 0.4 |
| Salicylic acid USP | 0.18 | 0 | 0.15 | 0.17 | 0 | 0.18 | 0 |
| Benzoic acid | 0 | 0.05 | 0 | 0.1 | 0 | 0 | 0 |
| Glycerin | 7 | 0 | 3 | 5 | 0 | 0 | 0 |
| Sorbitol | 0 | 5 | 3 | 3 | 0 | 0 | 0 |
| Briquest ADPA-60AW (HEDP) | 0.05 | 0.1 | 0.05 | 0 | 0 | 0 | 0 |
| Benzyl alcohol | 1.5 | 2.5 | 2.0 | 3 | 3 | 3 | 3 |
| Hydrogen peroxide | 0.5 | 0.5 | 1.0 | 2 | 0.5 | 0.5 | 0.5 |
| pH (adjusted by NAOH) | 3.0 | 3.5 | 3.0 | 3.0 | 2.5 | 2.5 | 2.5 |
| Total | 100.00 | 100.00 | 100.00 | 100.00 | 100.00 | 100.00 | 100.00 |

Solutions U, V, W, X can be used in topical applications and solutions Y, Z, Z1 can be used as hard surface disinfectants.

Example XV

Solutions Z2 and Z3 along with their activities against *M. terrae* using ASTM E2111 are summarized in Table XV below. Only Solution Z2 is in accordance with the present invention.

TABLE XV

| Ingredient | Z2 % w/w | Z3 % w/w |
|---|---|---|
| Deionized water | Up to 100 | Up to 100 |
| Phosphoric acid (75%) | 0.15 | 0.15 |
|  | 0.11 | 0.11 |
| Briquest ADPA-60AW (60%) | 0.48 | 0.48 |
|  | 0.29 | 0.29 |
| C6 Dowfax hydrotrope (40%) | 0.18 | 0.18 |
|  | 0.07 | 0.07 |
| Biosoft S-100 (98%) | 0.18 | 0.18 |
|  | 0.18 | 0.18 |
| Ethal OA-23 (70%) | 0.08 | 0.08 |
|  | 0.05 | 0.05 |
| Hydrogen peroxide (50%) | 1.10 | 1.10 |
|  | 0.55 | 0.55 |
| Salicylic acid | 0.18 | 0.00 |
|  | 0.18 | 0.00 |
| pH (adjusted by adding KOH) | 1.8 | 1.8 |
| *M. terrae*, ASTM E2111, 5 min. contact time | >6 LR | <1 LR |

The active concentration in solution is shown in bold in the second row corresponding to each ingredient.

As can be seen in Table XV above, salicylic acid contributes to efficacy against *M. Terrae* under the conditions of the ASTM E2111 test methodology and at a contact time of 5 minutes.

Example XVI

Additional solutions according to the present invention are summarized in Tables XVIa and XVIb below.

TABLE XVIa

| Ingredient | Z4 % w/w | Z5 % w/w | Z6 % w/w | Z7 % w/w |
|---|---|---|---|---|
| Deionized water | Up to 100 | Up to 100 | Up to 100 | Up to 100 |
| Phosphoric acid (75%) | 0.5 | 0.5 | 0.5 | 0.5 |
|  | 0.375 | 0.375 | 0.375 | 0.375 |
| Citric acid | 0 | 0.4 | 0.4 | 0.4 |
|  | 0 | 0.4 | 0.4 | 0.4 |
| C6 Dowfax hydrotrope (40%) | 0.18 | 0.18 | 0.18 | 0.18 |
|  | 0.07 | 0.07 | 0.07 | 0.07 |
| Biosoft S-100 (98%) | 0.18 | 0.18 | 0.18 | 0.18 |
|  | 0.18 | 0.18 | 0.18 | 0.18 |
| Ethal OA-23 (70%) | 0.08 | 0.08 | 0.08 | 0.08 |
|  | 0.05 | 0.05 | 0.05 | 0.05 |
| Hydrogen peroxide (50%) | 1.00 | 1.00 | 1.00 | 1.00 |
|  | 0.50 | 0.50 | 0.50 | 0.50 |
| Salicylic acid | 0.18 | 0.18 | 0 | 0.09 |
|  | 0.18 | 0.18 | 0 | 0.09 |
| Benzyl alcohol | 3.1 | 3.1 | 3.1 | 3.1 |
|  | 3.1 | 3.1 | 3.1 | 3.1 |
| pH (adjusted by adding KOH) | 3 | 2 | 2 | 2.5 |

The active concentration in solution is shown in bold in the second row corresponding to each ingredient.

TABLE XVIb

| Ingredient | Z8 % w/w |
|---|---|
| Deionized water | To 100 |
| Briquest ADPA-60AW (60%) | 0.5 |
|  | 0.35 |
| Phosphoric acid (75%) | 0.5 |
|  | 0.38 |

TABLE XVIb-continued

| Ingredient | Z8<br>% w/w |
|---|---|
| Cobratec 35-G (35% benzotriazole) | 0.1 |
| | 0.035 |
| 2-Furoic acid (99%) | 2.5 |
| | 2.48 |
| hydrogen peroxide (50%) | 4.0 |
| | 2.0 |
| Bioterge PAS 8S | 0.5 |
| Antifoam C | 0.006 |
| KOH | Up to pH = 3 |

The active concentration in solution is shown in bold in the second row corresponding to each ingredient.

Solutions Z2 and Z4 to Z7 can be used as hard surface disinfectants and solution Z8 can be used as a medical device disinfectant.

The foregoing examples are for illustrative purposes only and shall not be construed so as to restrict the scope of the invention as defined by the following claims.

We claim:

1. An aqueous disinfecting solution having a pH of from 0.6 to 7 consisting of:
   (a) hydrogen peroxide in a concentration of from 0.01 to 6% w/w;
   (b) benzyl alcohol in a concentration of from 1.5 to 4% w/w;
   (c) at least one anionic surfactant selected from the group consisting of (i) C8-C16 alkyl benzene sulfonic acids and alkali metal, alkaline earth metal, ammonium or alkylamine salts thereof; (ii) C8-C18 alkyl sulfonic acid; (iii) C6-C12 alkyl diphenyl oxide sulfonate surfactants, and (iv) alkyl or alkenyl esters or diesters of sulfosuccinic acid in which the alkyl or alkenyl groups independently contain from six to eighteen carbon atoms and alkali metal, ammonium, calcium and magnesium salts thereof in a concentration of from 0.01 to 10% w/w;
   (d) optionally, at least one ingredient chosen from 2-furan carboxylic acid, salicylic acid and benzoic acid in a concentration of from 0.01 to 8% w/w;
   (e) optionally, at least one nonionic surfactant selected from the group consisting of (i) ethoxylated alcohols; (ii) alkylglycosides having a hydrophile lyophile balance from 5 to 15; and (iii) a water-soluble block copolymer of ethylene oxide and propylene oxide, in a concentration of from 0.005 to 3% w/w;
   (f) optionally, at least one pH buffer or pH adjuster to achieve the desired pH value;
   (g) optionally, at least one corrosion inhibitor in a concentration of from 0.001 to 15% w/w;
   (h) optionally, at least one hydrotope selected from the group consisting of sodium xylene sulfonate, sodium cumene sulfonate, and sodium toluene sulfonate in a concentration of from 0.01 to 15% w/w;
   (i) optionally, at least one solvent selected from the group consisting of glycols, glycol ethers, n-butanol, n-butyl acetate, diisobutyl ketone, isobutanol, isobutyl acetate, isopropanol (anhydrous), isopropyl acetate, methyl isobutyl carbinol, methyl isobutyl ketone, primary amyl acetate mixed isomers, n-propanol, n-propyl acetate, n-butyl propionate, n-pentyl propionate, ethanol, propyl alcohol, isopropyl alcohol, and glycerin in a concentration of from 0.1 to 20% w/w;
   (j) optionally, at least one cation sequestering agent in a concentration of from 0.01 to 6% w/w;
   (k) optionally, at least one ingredient selected from the group consisting of silicone-based antifoaming agents, hydrogen peroxide stabilizers, thickeners, dyes, fragrances, and skin conditioning agents; and
   (l) water q.s. to 100% w/w;
   wherein all concentration values are based on the total weight of the solution and the solution is effective in destroying mycobacteria.

2. The solution of claim 1, wherein at least one of 2-furan carboxylic acid, salicylic acid and benzoic acid is present.

3. The solution of claim 1, wherein at east one of said non-ionic surfactants is present.

4. The solution of claim 1, wherein at least one cation seguestering agent is present.

5. The solution of claim 1, wherein at least one pH buffer or pH adjuster is present.

6. A solution according to claim 1, wherein the at least one pH buffer is selected from the group consisting of phosphoric acid, citric acid, glycolic acid, sodium carbonate, calcium carbonate, potassium hydroxide, sodium hydroxide, ethanolamine and lactic acid.

7. The solution of claim 1, wherein at least one corrosion inhibitor is present.

8. A solution according to claim 1, wherein the at least one corrosion inhibitor is selected from the group consisting of 1,2,3 benzotriazole, sodium molybdate, sodium nitrite, sodium bisulfate, sodium metabisulfate, chromates, borates, phosphates, polyphosphates, sodium benzoate, sodium gluconate and sodium silicate.

9. The solution of claim 1, wherein at least one of said hydrotopes is present.

10. The solution of claim 1, wherein at least one of said solvents is present.

11. The solution of claim 1, wherein at least one ingredient selected from the group consisting of hydrogen peroxide stabilizers, thickeners, and skin conditioning agents is present.

12. The solution of claim 1 wherein said hydrogen peroxide is present in a concentration of from 0.25 to 4% w/w.

13. The solution of claim 1, wherein the at least one nonionic surfactant is selected from the group consisting of a water-soluble block copolymer of ethylene oxide and propylene oxide, and a C6-C10 alkyl, 3.5 moles of ethylene oxide (EO) alcohol ethoxylate.

14. The solution of claim 1, having a pH of from 0.6 to 5.

15. A concentrated, aqueous, acidic disinfecting solution which can be diluted with water to provide a solution having a pH from 0.6 to 7 consisting of:
   (a) hydrogen peroxide in a concentration of from 0.01 to 6% w/w;
   (b) benzyl alcohol in a concentration of from 1.5 to 4% w/w;
   (c) at least one anionic surfactant selected from the group consisting of (i) C8-C16 alkyl benzene sulfonic acids and alkali metal, alkaline earth metal, ammonium or alkylamine salts thereof; (ii) C8-C18 alkyl sulfonic acid; (iii) C6-C12 alkyl diphenyl oxide sulfonate surfactants, and (iv) alkyl or alkenyl esters or diesters of sulfosuccinic acid in which the alkyl or alkenyl groups independently contain from six to eighteen carbon atoms and alkali metal, ammonium, calcium and magnesium salts thereof in a concentration of from 0.01 to 10% w/w;
   (d) optionally, at least one ingredient chosen from 2-furan carboxylic acid, salicylic acid and benzoic acid in a concentration of from 0.01 to 8% w/w;

(e) optionally, at least one nonionic surfactant selected from the group consisting of (i) ethoxylated alcohols; (ii) alkylglycosides having a hydrophile lyophile balance from 5 to 15; and (iii) a water-soluble block copolymer of ethylene oxide and propylene oxide, in a concentration of from 0.005 to 3% w/w;

(f) optionally, at least one pH buffer or pH adjuster to achieve the desired pH value;

(g) optionally, at least one corrosion inhibitor in a concentration of from 0.001 to 15% w/w;

(h) optionally, at least one hydrotrope selected from the group consisting of sodium xylene sulfonate, sodium cumene sulfonate, and sodium toluene sulfonate in a concentration of from 0.01 to 15% w/w;

(i) optionally, at least one solvent selected from the group consisting of glycols, glycol ethers, n-butanol, n-butyl acetate, diisobutyl ketone, isobutanol, isobutyl acetate, isopropanol (anhydrous), isopropyl acetate, methyl isobutyl carbinol, methyl isobutyl ketone, primary amyl acetate mixed isomers, n-propanol, n-propyl acetate, n-butyl propionate, n-pentyl propionate, ethanol, propyl alcohol, isopropyl alcohol, and glycerin in a concentration of from 0.1 to 20% w/w;

(j) optionally, at least one cation sequestering agent in a concentration of from 0.01 to 6% w/w;

(k) optionally, at least one ingredient selected from the group consisting of silicone-based antifoaming agents, hydrogen peroxide stabilizers, thickeners, dyes, fragrances, and skin conditioning agents; and (l) water q.s. to 100% w/w;

wherein all concentration values are based on the total weight of the solution and the solution is effective in destroying mycobacteria.

16. A method of killing mycobacteria comprising applying an aqueous disinfecting solution to a surface contaminated with mycobacteria, the solution having a pH of from 0.6 to 7 and consisting of:

(a) hydrogen peroxide in a concentration of from 0.01 to 6% w/w;

(b) benzyl alcohol in a concentration of from 1.5 to 4% w/w;

(c) at least one anionic surfactant chosen from (i) C8-C16 alkyl benzene sulfonic acids and alkali metal, alkaline earth metal, ammonium or alkylamine salts thereof; (ii) C8-C18 alkyl sulfonic acid; (iii) C6-C12 alkyl diphenyl oxide sulfonate surfactants, and (iv) alkyl or alkenyl esters or diesters of sulfosuccinic acid in which the alkyl or alkenyl groups independently contain from six to eighteen carbon atoms and alkali metal, ammonium, calcium and magnesium salts thereof in a concentration of from 0.01 to 10% w/w;

(d) optionally, at least one ingredient chosen from 2-furan carboxylic acid, salicylic acid and benzoic acid in a concentration of from 0.01 to 8% w/w;

(e) optionally, at least one nonionic surfactant selected from the group consisting of (i) ethoxylated alcohols; (ii) alkylglycosides having a hydrophile lyophile balance from 5 to 15; and (iii) a water-soluble block copolymer of ethylene oxide and propylene oxide, in a concentration of from 0.005 to 3% w/w;

(f) optionally, at least one pH buffer or pH adjuster to achieve the desired pH value;

(g) optionally, at least one corrosion inhibitor in a concentration of from 0.001 to 15% w/w;

(h) optionally, at least one hydrotrope selected from the group consisting of sodium xylene sulfonate, sodium cumene sulfonate, and sodium toluene sulfonate in a concentration of from 0.01 to 15% w/w;

(i) optionally, at least one solvent selected from the group consisting of glycols, glycol ethers, n-butanol, n-butyl acetate, diisobutyl ketone, isobutanol, isobutyl acetate, isopropanol (anhydrous), isopropyl acetate, methyl isobutyl carbinol, methyl isobutyl ketone, primary amyl acetate mixed isomers, n-propanol, n-propyl acetate, n-butyl propionate, n-pentyl propionate, ethanol, propyl alcohol, isopropyl alcohol, and glycerin in a concentration of from 0.1 to 20% w/w;

(j) optionally, at least one cation sequestering agent in a concentration of from 0.01 to 6% w/w;

(k) optionally, at least one ingredient selected from the group consisting of silicone-based antifoaming agents, hydrogen peroxide stabilizers, thickeners, dyes, fragrances, and skin conditioning agents; and (l) water q.s. to 100% w/w;

wherein all concentration values are based on the total weight of the solution and the solution is effective in destroying mycobacteria.

17. The method of claim 16, wherein the solution is circulated in place through equipment to be disinfected at a temperature of from 20 to 60 degrees Celsius to disinfect the equipment.

18. A multi-component system which can be combined to provide a disinfecting solution according to claim 1.

* * * * *